(12) United States Patent
Chen et al.

(10) Patent No.: US 12,268,529 B2
(45) Date of Patent: Apr. 8, 2025

(54) SYSTEMS AND METHODS FOR TOUCHLESS DETECTION OF HEART RATE VARIABILITY

(71) Applicant: WISTRON CORPORATION, New Taipei (TW)

(72) Inventors: Yin-Yu Chen, New Taipei (TW); Kai Jen Cheng, New Taipei (TW); Yao-Tsung Chang, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 219 days.

(21) Appl. No.: 18/053,560

(22) Filed: Nov. 8, 2022

(65) Prior Publication Data

US 2024/0156413 A1 May 16, 2024

(51) Int. Cl.
| | | |
|---|---|---|
| A61B 5/00 | (2006.01) | |
| A61B 5/024 | (2006.01) | |
| A61B 5/0245 | (2006.01) | |
| A61B 5/05 | (2021.01) | |
| A61B 5/11 | (2006.01) | |

(52) U.S. Cl.
CPC ........ *A61B 5/7267* (2013.01); *A61B 5/02405* (2013.01); *A61B 5/05* (2013.01); *A61B 5/1102* (2013.01); *A61B 5/1128* (2013.01); *A61B 5/0245* (2013.01)

(58) Field of Classification Search
CPC ..... A61B 5/7267; A61B 5/02405; A61B 5/05; A61B 5/1102; A61B 5/1128; A61B 5/0245; A61B 5/0507
See application file for complete search history.

(56) References Cited

U.S. PATENT DOCUMENTS

2003/0212336 A1* 11/2003 Lee ...................... A61B 5/7207
600/504
2021/0244339 A1* 8/2021 Szabados ............... A61B 5/352

OTHER PUBLICATIONS

Iyer et al. 2022 Sensors 22:3106 20 pages (Year: 2022).*
Ho 2021 Ms thesis Electro-Optical Engineering National Chio Tung University Taiwan 87 pages (Year: 2021).*
Tsai et al. 2020 IEEE Xplore 2020 42nd Annual International Conference of the IEEE Engineering in Medicine & Biology Society EMBC p. 232-235 (Year: 2020).*
Shi et al. 2021 Nature â Scientific Reports 11:3025 13 pages (Year: 2021).*

* cited by examiner

*Primary Examiner* — Keith M Raymond
*Assistant Examiner* — Patrick M Mehl
(74) *Attorney, Agent, or Firm* — Peigen Jiang; Greenberg Traurig, LLP (57) ABSTRACT

An apparatus and a method for detecting heartbeat include a sensor configured to detect displacements of an object without contacting the object wherein the object displaces corresponding the a human's heartbeat, a data processing unit configured to extract a feature dataset from the detected displacement data, and a neural network configured to inference inter beat intervals from the extracted feature dataset using a pre-trained model.

20 Claims, 13 Drawing Sheets

SYSTEMS AND METHODS FOR TOUCHLESS DETECTION OF HEART RATE VARIABILITY

BACKGROUND

The present disclosure relates generally to the field of heart rate variability detection, and, more particularly, to touchless detection of the heart rate variability.

Heart rate variability (HRV) is a method to measure the degree of continuous heart rate variation. Currently, the HRV is mainly used in clinical practice to analyze the state of autonomic balance. Electrocardiogram (ECG) or photoplethysmogram (PPG) are two mature technology for measuring HRV. ECG measures heartbeat-to-heartbeat interval, while PPG measures pulse-to-pulse interval. They are collectively called inter beat interval (IBI). Entering the IBI over a period of time into standard HRV calculation formula can obtain various HRV indicators.

The ECG or PPG method, however, requires electrode pads to be attached to human skin or to be made into a wearable device such as a chest strap, wrist ring or ear loop. They all require a physical contact, and thus are not convenient.

As such, what is desired is contactless systems and methods to measure HRV.

SUMMARY

A method for detecting heartbeat includes detecting displacements of an object by a sensor not contacting the object, wherein the object displaces corresponding to a human's heartbeat, extracting a feature dataset from the detected displacement data, and inferencing inter beat intervals from the extracted feature dataset by a first neural network using a pre-trained model.

In embodiments, the sensor is a radar unit configured to transmit a radio wave on the object and detect a reflection of the radio wave.

In embodiments, the inferencing inter beat intervals includes detecting peak times in the feature dataset by the first neural network searching for patterns of the model in the feature dataset.

In embodiments, the first neural network and the model reside in a remote data center.

In embodiments, the model is developed by a second neural network by comparing peak times extracted from the feature dataset with peak times measured by an electrocardiogram (ECG) measurement on the object, wherein the first and second neural network are of the same type.

In embodiments, the feature dataset is organized into a first and second predetermined detection zone overlapped by a predetermined duration.

The drawings accompanying and forming part of this specification are included to depict certain aspects of the disclosure. A clearer conception of the disclosure, and of the components and operation of systems provided with the disclosure, will become more readily apparent by referring to the exemplary, and therefore non-limiting, embodiments illustrated in the drawings, wherein like reference numbers (if they occur in more than one view) designate the same elements. The disclosure may be better understood by reference to one or more of these drawings in combination with the description presented herein.

DESCRIPTION

The present disclosure relates to systems and methods for contactless measuring heart rate variability (HRV). Such systems and methods rely on contactless sensors such as radar, low energy laser beam or ultrasound to detect chest displacement of a living creature, and then use data processing to extract inter-beat-interval (IBI) data for the HRV calculation. In embodiments of the present disclosure, the living creature mentioned herein is human, but the present disclosure is not limited thereto. In another embodiment of the present disclosure, the living creature may be a pet, or a livestock.

However, the human's chest displacement are a result of both respiration and heartbeat. In fact, respiration causes far greater chest displacement than heartbeat does. In addition, there are signal interference and signal-to-noise ratio being very low, therefore, separating heartbeat wave signal from respiration wave signal is a challenge.

The present disclosure proposes a two-step process to obtain the IBI from a contactless measurement data. A first step is to extract heartbeat wave data from raw measurement data using a numerical differentiation algorithm. As respiration wave signal is noise to heartbeat wave signal, this step basically increases heartbeat/respiration signal-to-noise ratio (SINR). The second step is to enter the heartbeat wave signal to an artificial intelligent trained model to extract IBI.

Figure 1:
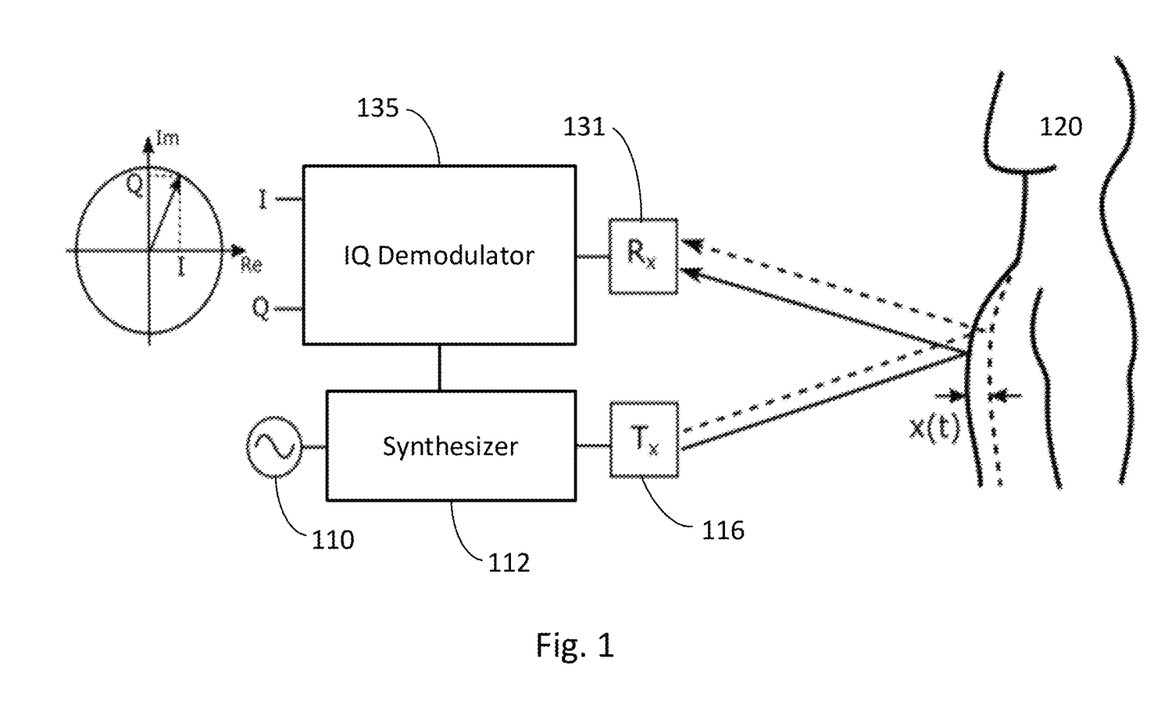
FIG. 1 illustrates a contactless HRV measurement system according to an embodiment of present disclosure.

FIG. 1 illustrates a contactless HRV measurement system according to an embodiment of present disclosure. The measurement system employs an exemplary radar system with a radio wave generator 110, a synthesizer 112, a transmitter 116, a receiver 131 and an IQ demodulator. The transmitter 116 projects a radar signal onto a human 120's chest which reflects some of the radar signal back to the receiver 131. If the chest moves either toward or away from the transmitter, there will be a slight change in the frequency of the radio waves received by the receiver 131 due to the Doppler effect. The IQ demodulator generates an I and Q waveforms resulting from quadrature demodulation. The I and Q waveforms are equivalent to the real and imaginary parts of a complex number. In embodiments of the present disclosure, the radar system may be an FMCW radar, or a continuous wave (CW) radar. Descriptions are made below by using a CW radar as an example.

The way of converting IQ signal to phase and amplitude can be non-linear, linear (project to I or Q-axis) or direct arctangent demodulation. The non-linear method mainly removes the DC level first, then uses the Arctangent extract phase, and finally uses phase unwrapping to calculate the displacement of the test body, which is the chest displacement of a human under test. The displacement calculated by linear and direct arctangent conversion is a relative displacement rather than an absolute displacement. An advantage is that the error of DC removal is reduced, and the time to find the peak is sufficient.

After the Phase and Amplitude are extracted, numerical difference is used to find heart rate characteristics. The numerical difference method can be one-order difference, multi-order difference, central-difference, backward-difference, Forward-difference and others.

Figure 2:
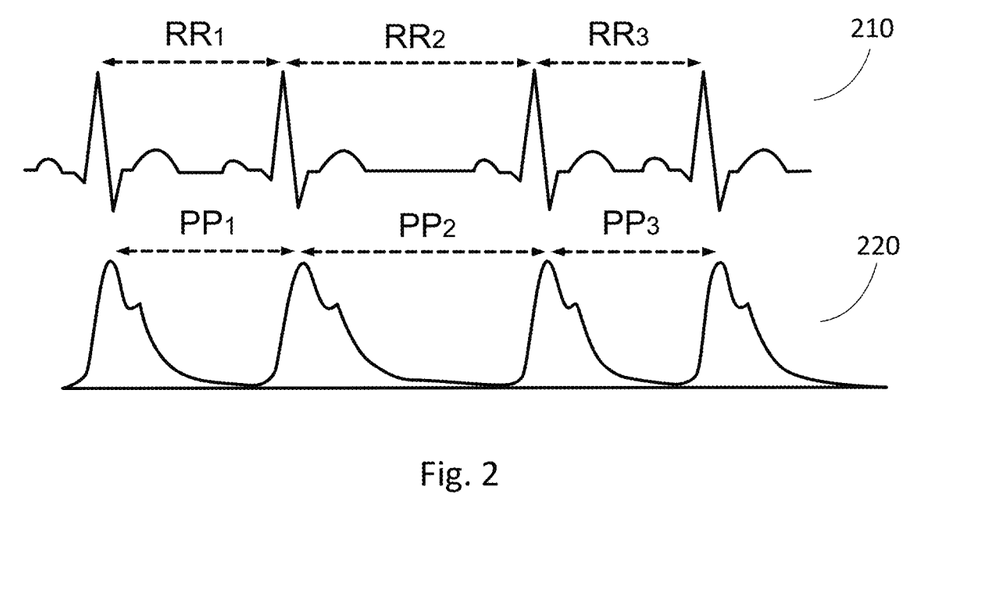
FIG. 2 illustrates ECG and PPG measurement data. Plot 210 reflects data from an ECG measurement.

FIG. 2 illustrates ECG and PPG measurement data. Plot 210 reflects data from an ECG measurement. Instantaneous heart rate can be calculated on the basis of the R-R interval from one complex to the next. An average rate can be taken by counting the number of depolarizations within 6 seconds and multiplying by ten. Where the rhythm is very irregular, a more accurate rate may be obtained by counting over 12 seconds. Plot 220 reflects data from a PPG measurement. Heart rate can be similarly calculated on the basis of the P-P interval from one complex to the next.

The mean value of RR intervals (millisecond) and Mean heart rate (bpm) are defined by $\overline{RR}=1/N\Sigma_{j=1}^{N}RR_j$ and $$\overline{RR} = \frac{1}{N}\sum_{j=1}^{N} RR_j \text{ and } \overline{HR} = \frac{1}{\overline{RR}},$$

respectively.

Standard Deviation of Normal Heartbeat Intervals (SDNN) can be obtained from following equation (millisecond):

$$SDNN = \sqrt{\frac{1}{N-1}\sum_{j=1}^{N}(RR_j - \overline{RR})^2}$$

The average normal heartbeat interval for a short period of time, such as five minutes, can be calculated first, and then the average standard deviation of for the whole period (SDANN index in millisecond) can be calculated from the following equation:

$$SDANN = \sqrt{\frac{1}{N-1}\sum_{j=1}^{N}(RR_{5j} - \overline{RR_5})^2}$$

Alternatively, standard deviation of normal heartbeat interval of every five minutes can be calculated first, and then an average standard deviation for the whole period (SDNN index in millisecond) can be obtained from the following equation:

$$SDANNindex = \frac{1}{N}\sum_{j=1}^{N} SDNN_{5j}$$

Root mean square of the sum of squares of normal heartbeat interval differences (RMSSD) is calculated from below equation (in millisecond):

$$RMSSD = \sqrt{\frac{1}{N-1}\sum_{j=1}^{N-1}(RR_{j+1} - RR_j)^2}$$

A percentage of neighboring normal heartbeat interval differences that exceeds 50 millisecond (pNN50) is calculated from following equation, wherein NN50 represents a number of normal heartbeat differences that exceeds 50 millisecond.

$$pNN50 = \frac{NN50}{N-1} \times 100\%$$

Figure 3:
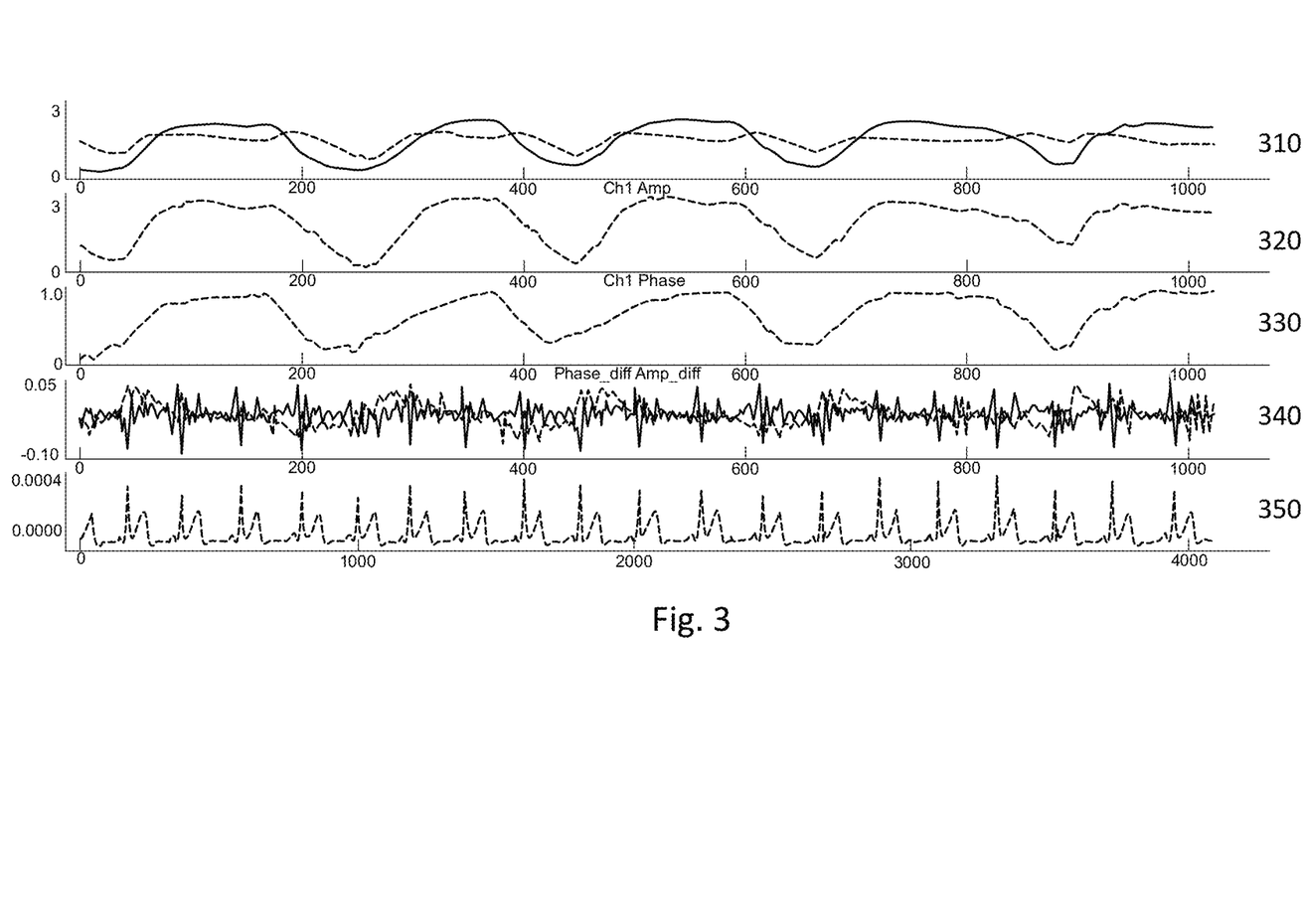
FIG. 3 illustrates radar measurement data along with ECG measurement data.

FIG. 3 illustrates radar measurement data along with ECG measurement data. Plot 310 reflects outputs, I and Q, from the IQ demodulator 135 of FIG. 1. Plot 320 reflects an amplitude (A) derived from the plot 310 according to following equation (1).

$$A = \sqrt{I^2 + Q^2} \qquad \text{Eq. (1)}$$

Plot 330 reflects a phase (φ) derived from the plot 310 according to following equation (2).

$$\varphi(t) = \arctan\left(\frac{B_Q(t)}{B_I(t)}\right) = \arctan\left(\frac{V_Q + A_r\sin(\theta + \frac{4\pi\Delta x(t)}{\lambda})}{V_I + A_r\cos(\theta + \frac{4\pi\Delta x(t)}{\lambda})}\right) \qquad \text{Eq. (2)}$$

Plot 340 reflects numerical differentiation processed amplitude (A) and phase (p) data plotted together. The processed amplitude (A) is a line that shows periodic sharp spikes; and the processed phase (p) is a line that shows irregular a waveform.

Plot 350 reflects an ECG measurement data. The ECG measurement is conducted on the same person at the same time. As shown in FIG. 3, the peaks of the ECG plot more or less coincide with spikes of the processed amplitude (A) line.

Figure 4:
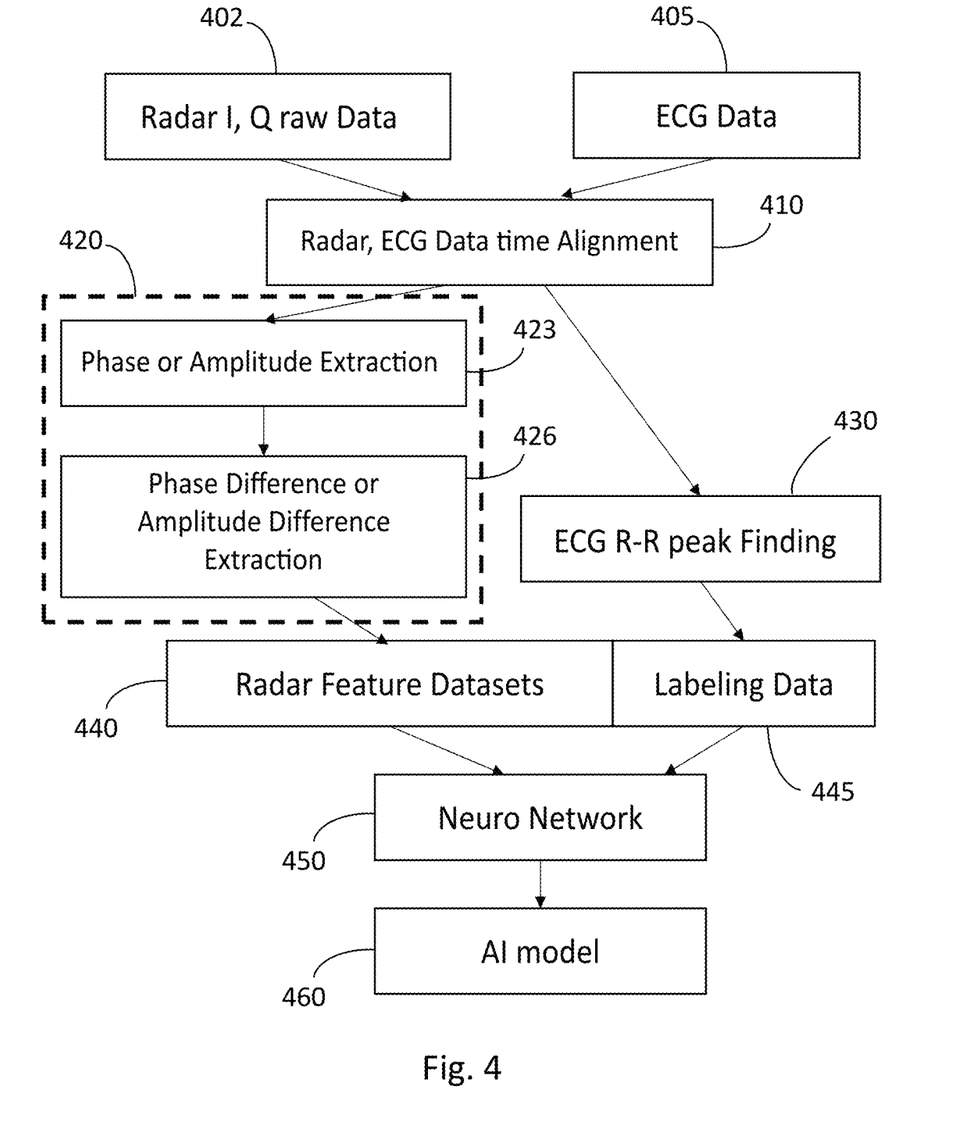
FIG. 4 is a flowchart illustrating a model generating process for a contactless measurement of HRV according to embodiment of the present disclosure.

FIG. 4 is a flowchart illustrating a model generating process for a contactless measurement of HRV according to an embodiment of the present disclosure. As an example, the contactless sensor is a radar system. The process begins with receiving both radar measured I, Q raw data in block 402 and ECG measured data in block 405. The radar measurement and the ECG measurement are synchronously performed on the same person, i.e., the data sampling of both measurements are time aligned in block 410. The alignment process includes a rough estimation from body motion signals either automatically or manually. Then the alignment is fine-tuned manually.

The radar measurement data is then processed by a data processing module 420 that includes phase or amplitude extraction 423 and phase difference or amplitude difference extraction 426 to create radar feature datasets 440. One dimensional raw data, e.g., amplitude, phase, amplitude difference, and phase difference are converted to two dimensional feature map, such as two channels of amplitude difference with a 512 length (sample) (512, 2) becoming reshaped (32, 16, 2), (16, 32, 2), (64, 8, 2) or (32, 8, 4), . . . and dual (512, 2) becoming reshaped (32, 16, 4) . . . .

At the same time, the ECG measurement data is processed in block 430 to find ECG R-R peaks to create labeling data 445 which will be used as IBI reference for subsequent artificial intelligent (AI) training. Both the radar feature datasets 440 and the ECG labeling data 445 are fed into a neuro network in block 450 to generate an AI model 460 for future radar measurement inferencing process.

In embodiments, the neutral network is a convolution neural network (CNN) that includes a convolution layer, a pooling layer, a flatten layer and a multilayer perceptron. The convolution layer provides core functions of the neural network including extracting features of the data. The pooling layer is a calculation method for retaining important features and is mainly used to reduce dimensionality. The flatten layer is used to flatten the output features of the convolution layer and the pooling layer, and perform dimension conversion.

The multilayer perceptron includes fully connected layers and a dropout layer. The fully connected layer which is so called a dense layer, is used to learn from the features of the data. Each neuron in the fully connected layer is fully connected to all the neurons in the previous layer. Fully connected layers can integrate class-discriminative local information in convolutional or pooling layers. In order to improve the performance of the CNN network, an activation function of each neuron in the fully connected layer generally adopts the ReLU function. An output value of the last fully connected layer is passed to an output. To solve the classification problem, softmax can be used for classification. This layer can also be called a softmax layer. If the application is a regression problem, a linear or non-linear activation function can be used.

Figure 5:
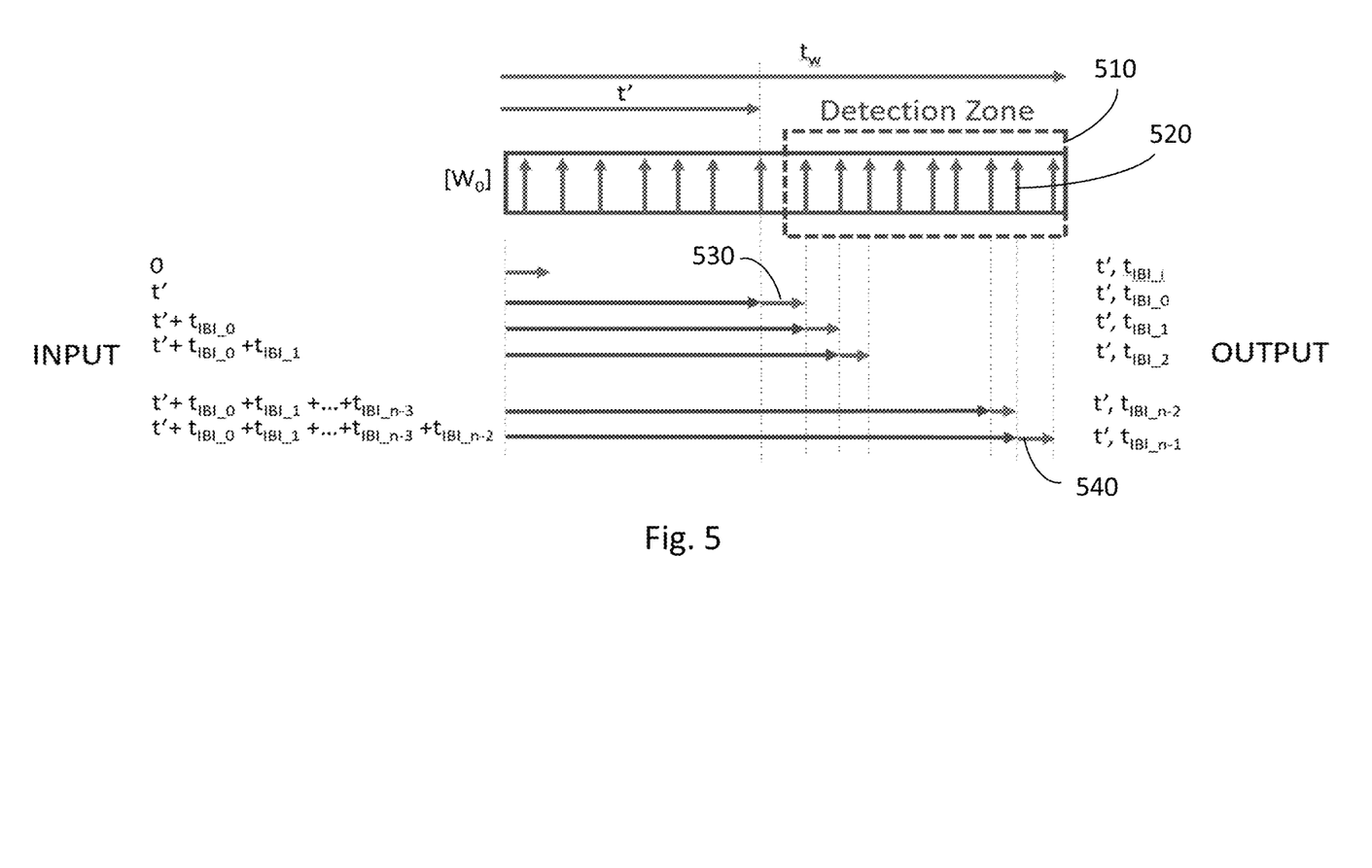
FIG. 5 illustrates steps performed by the neural network to detect inter beat intervals (IBI).

FIG. 5 illustrates steps performed by the neural network to detect inter beat intervals (IBI). A radar feature dataset Wo collected during a predetermined sampling time ($t_w$) is inputted to the neuro network. In embodiments, the sampling time $t_w$ is long enough to cover multiple ECG measurements or labels. For example, $t_w$ is 10 seconds. Within the predetermined sampling time $t_w$, a predetermined duration is chosen as a detection zone 510. In embodiments, the detection zone 510 also covers multiple ECG labels. For example, a duration of the detection zone 510 is 5 seconds. A peak detected right before the detection zone 510 occurs at a time t'. A next peak is detected at a time $t'+t_{IBI\_0}$, where $t_{IBI\_0}$ (530) is an inter beat interval. Subsequent peaks are detected similarly to obtain $t_{IBI\_i}$ until the last inter beat interval 540 within the detection zone. Each detected inter beat interval, $t_{IBI\_i}$ will be compared with the corresponding ECG measurements or labels which are used as references for calculating errors of the radar measurement system. The errors will be used by the neural network for learning.

Figure 6:
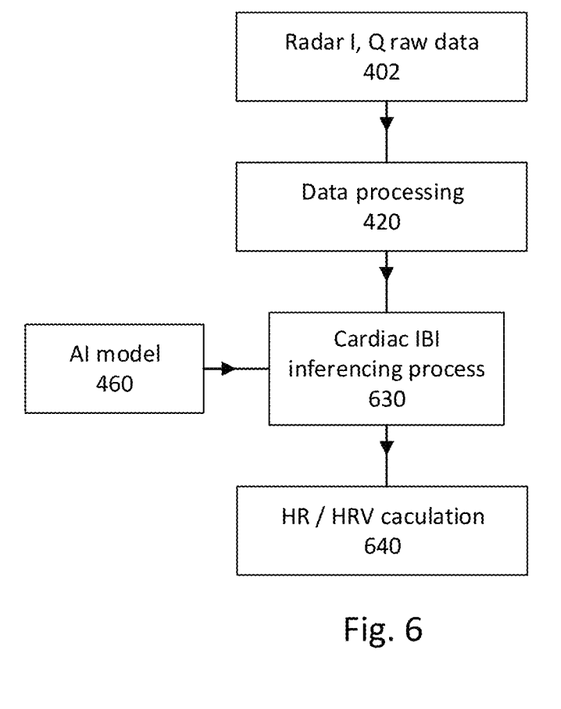
FIG. 6 is a flowchart illustrating a contactless measurement data inferencing process according to embodiments of the present disclosure.

FIG. 6 is a flowchart illustrating a contactless measurement data inferencing process according to embodiments of the present disclosure. Inference applies knowledge from a trained neural network model and a uses it to infer a result. So, when a new unknown dataset is input through a trained neural network, it outputs a prediction based on predictive accuracy of the neural network. Inference comes after training as it requires a trained neural network model.

As shown in FIG. 6, if the AI model 460 is generated with radar measurement data, the contactless measurement should use the same type of radar measurement system for perform data acquisition in block 402 and data processing in block 420. A cardiac IBI inferencing process module 630 employs the AI model 460 generated in the process shown in FIG. 4 to process the newly measured data from the data processing block 420. The AI model may contain data patterns trained from the training feature datasets. The same neural network used in the training process may also be used in the inferencing process. During the inference process, the AI machine looks for the data patterns in the radar measurement feature dataset and detects a peak time based on the recognized patterns. By using the AI model 460, the data inferencing process can overcome the low signal-to-noise ratio in the contactless measurement data due to the fact that human chest displacement is caused by both respiration and heartbeat.

After the inferencing process 630, the obtained cardiac IBI data is used for calculating heart rate and heart rate variability (HR/HRV) in block 640.

Figure 7:
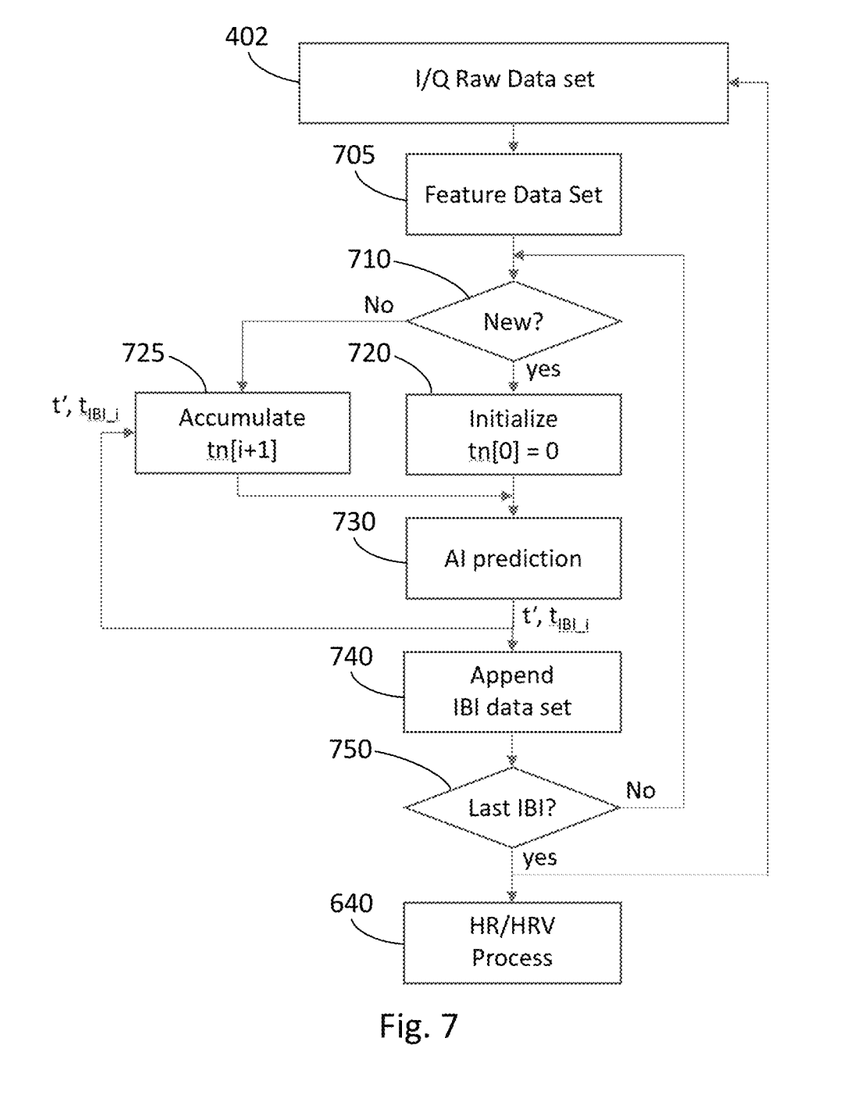
FIG. 7 is flowchart illustrating a data inferencing process according to an embodiment of the present disclosure.

FIG. 7 is flowchart illustrating a data inferencing process according to an embodiment of the present disclosure. The process begins with taking in a feature dataset for a particular person in block 705. If the process has just started, i.e., the feature dataset is new detected in block 710, the process enters block 720 by initializing a time mark tn[0] to zero. Then the process enters block 730 where AI prediction is performed on the feature dataset to detect the last peak time t' before a detection zone and an inter beat interval ($t_{IBI\_0}$) to a first peak time in the detection zone. An IBI dataset collects every peak time (($t_{IBI\_i}$) detected in the detection zone in block 740. If block 710 realizes that the feature dataset is not newly inputted, it will enter block 725 instead and accumulate the peak time after each detected peak time, i.e., $$tn[1] = t' + t_{IBI\_0}$$

$$tn[2] = t' + t_{IBI\_0} + t_{IBI\_1}$$

$$\ldots$$

$$tn[i+1] = t' + t_{IBI\_0} + t_{IBI\_1} + \ldots + t_{IBI\_i}$$

Referring again to FIG. 7, during each peak time detection cycle, the time mark tn[i] is read in block 750. If the time mark tn[i] has reached an end of the detection zone, the process will abort the peak time detection cycle and enter block 640 where a heart rate (HR) and a heart rate variation (HRV) for the person will be extracted from the IBI dataset.

Figure 8:
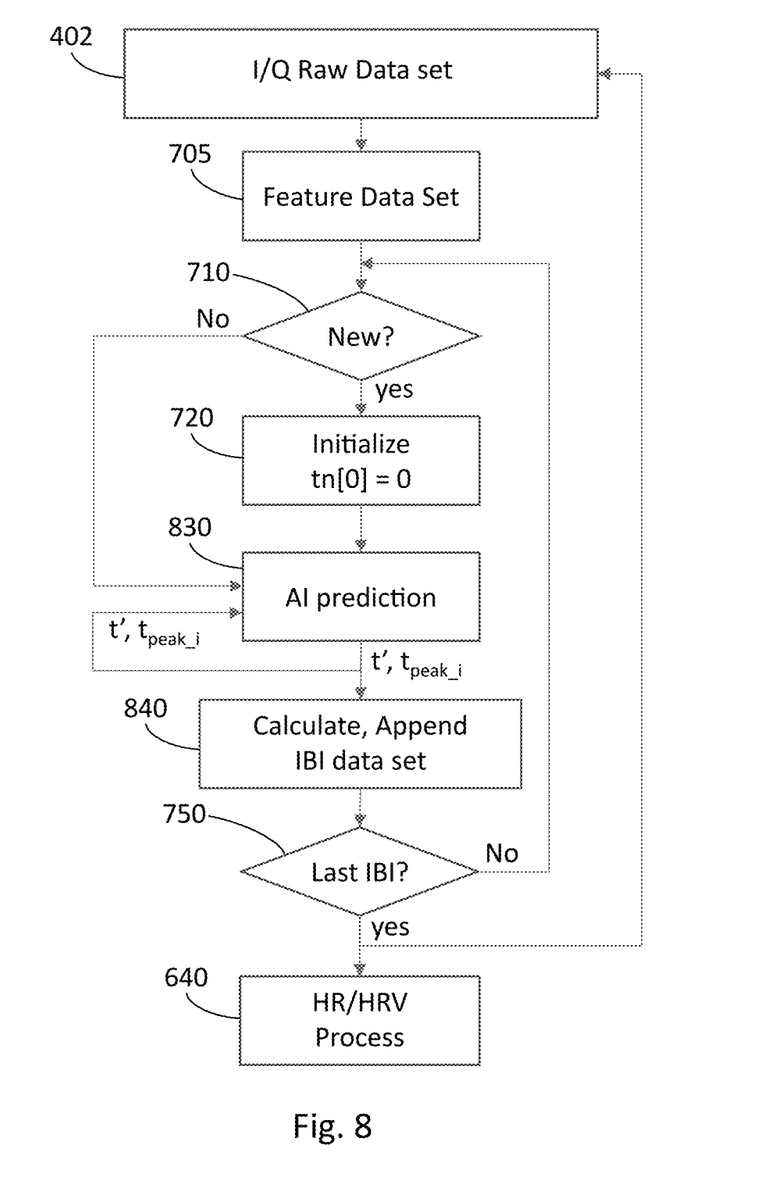
FIG. 8 is flowchart illustrating a data inferencing process according to another embodiment of the present disclosure.

FIG. 8 is flowchart illustrating a data inferencing process according to another embodiment of the present disclosure. The process shown in FIG. 8 executes an AI prediction block 830 and a calculating and appending to IBI dataset block 840 in place of blocks 730 and 740 shown in FIG. 7. In the block 830, the process shown in FIG. 8 detects each peak time within the detection zone ($t_{peak\_i}$) and a peak time (t') immediately before the detection zone which is referred to as a pilot peak. In embodiments, the pilot peak may be chosen at another peak time outside of the detection zone but within the data window. However, a first peak time within the data window is not preferred to be used as the pilot peak as the first peak time may fall on a boundary of the data window. Once the pilot peak (t') is determined during the training process, the inference process will first detect the pilot peak among the radar measurement feature dataset.

In block 840, the process calculates each IBI ($t_{IBI[i]}$) from the detected peak time by subtracting neighboring peak time values: $t_{IBI[i]} = t_{peak\_i} - t_{peak\_i-1}$. In block 840, the process also stores the calculated IBI in an IBI dataset as the process shown in FIG. 7 does.

Figure 9:
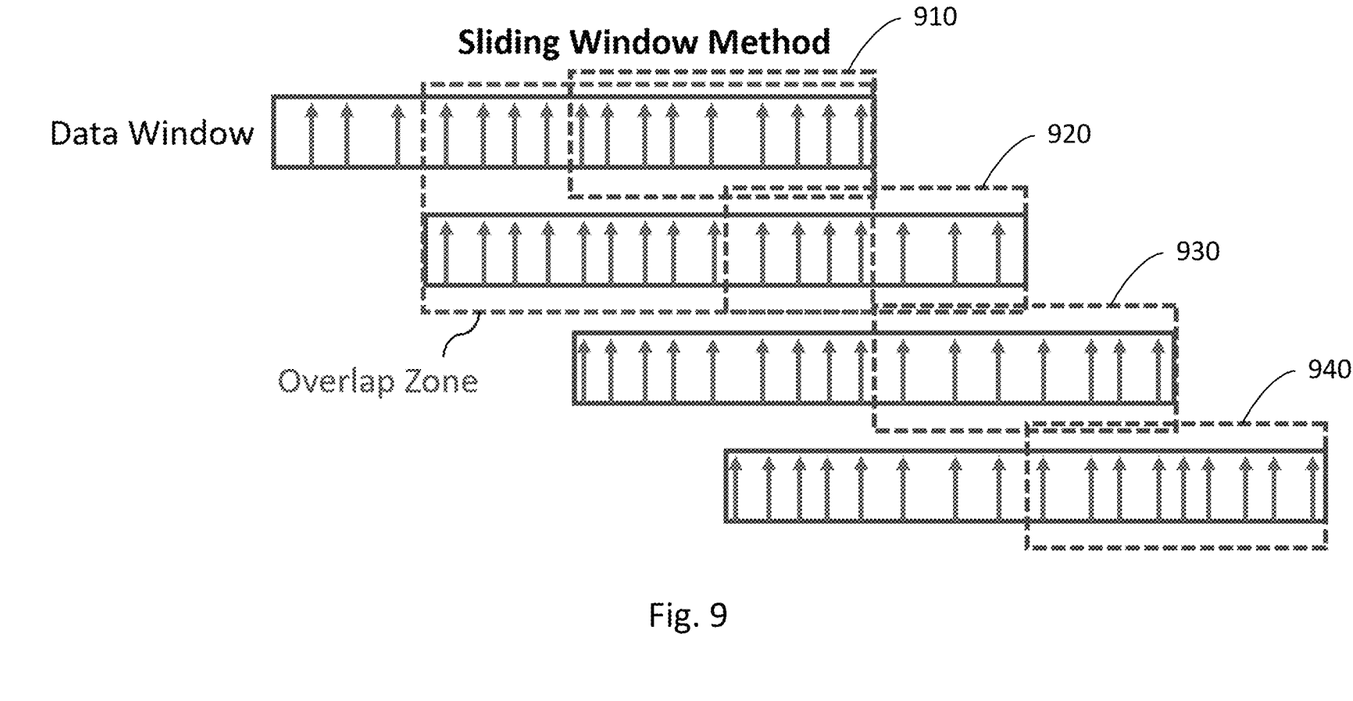
FIG. 9 illustrates a sliding window method for continuously detecting a human's IBI.

FIG. 9 illustrates a sliding window method for continuously detecting human IBI. In operations, human's heart rate variation (HRV) is often continuously monitored. In such cases, feature datasets are continuously inputted to the neural network for IBI detection. In embodiments, a next detection zone overlaps in time a current detection zone, so that the same sampling data are analyzed in both the current detection zone and the next detection zone to verify the AI model's accuracy. As shown in FIG. 9, a detection zone 920 has an overlap with a detection zone 910; a detection zone 930 has an overlap with the detection zone 920; and a detection zone 940 has an overlap with the detection zone 930. A duration of the overlaps can vary. As examples, the overlap between detection zones 910 and 920 or detection zones 930 and 940 covers four IBIs; and the overlap between detection zones 920 and 930 covers three IBIs. Alternatively, the detection zones does not overlap, so that more data can be analyzed quickly.

Figure 10:
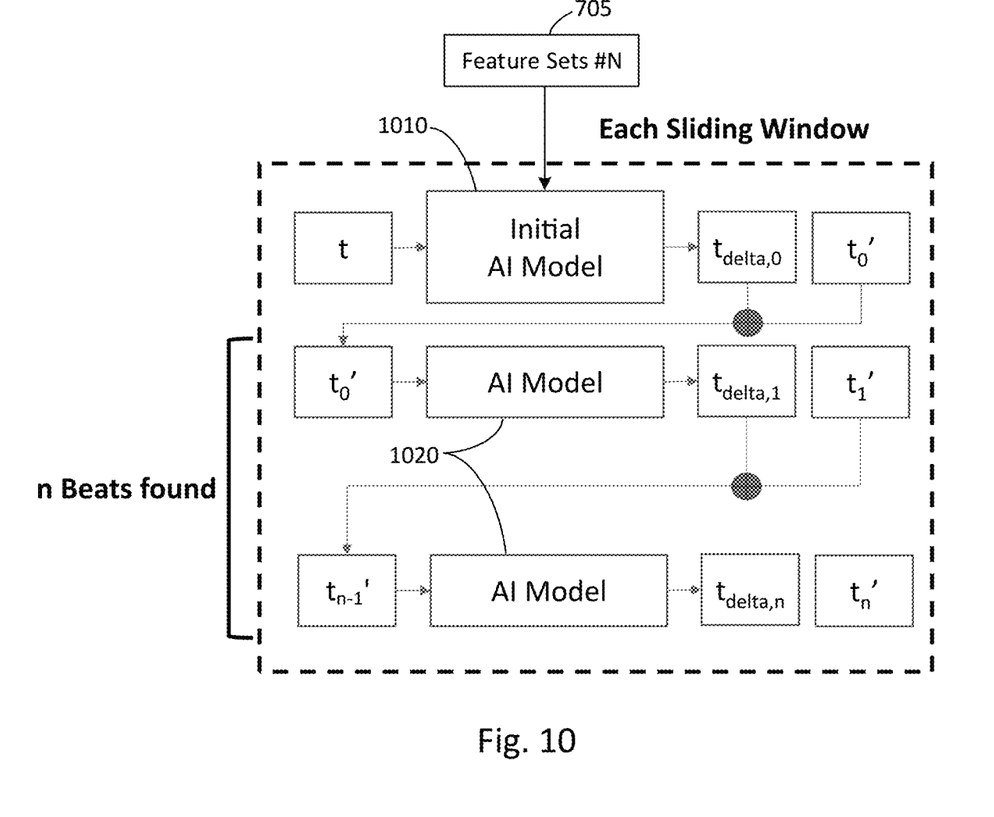
FIG. 10 is a block diagram corresponding to the data inferencing process shown in FIG. 7.

FIG. 10 is a block diagram corresponding to the data inferencing process shown in FIG. 7. As shown in FIG. 10, the feature dataset 705 is inputted to an initial AI model 1010 which detects a pilot peak time $t_0'$ immediately before a predetermined detection zone and a first inter-beat interval (IBI) $t_{delta,0}$ which is a time difference between a next peak time and the peak time $t_0'$. The initial AI model 1010 may be adjusted according to the experience in detecting the initial peak times, and an adjusted AI model 1020 may be used for detecting subsequent peak times. With a previous detected peak time as an input, the AI model 1020 detects subsequent peak times from the feature dataset. For example, the peak time $t_0'$ is inputted into the AI model 1020 which detects next peak times $t_1'$ and calculate a next IBI $t_{delta,1}$. Such process continues until all n beats are found in the detection zone.

Figure 11:
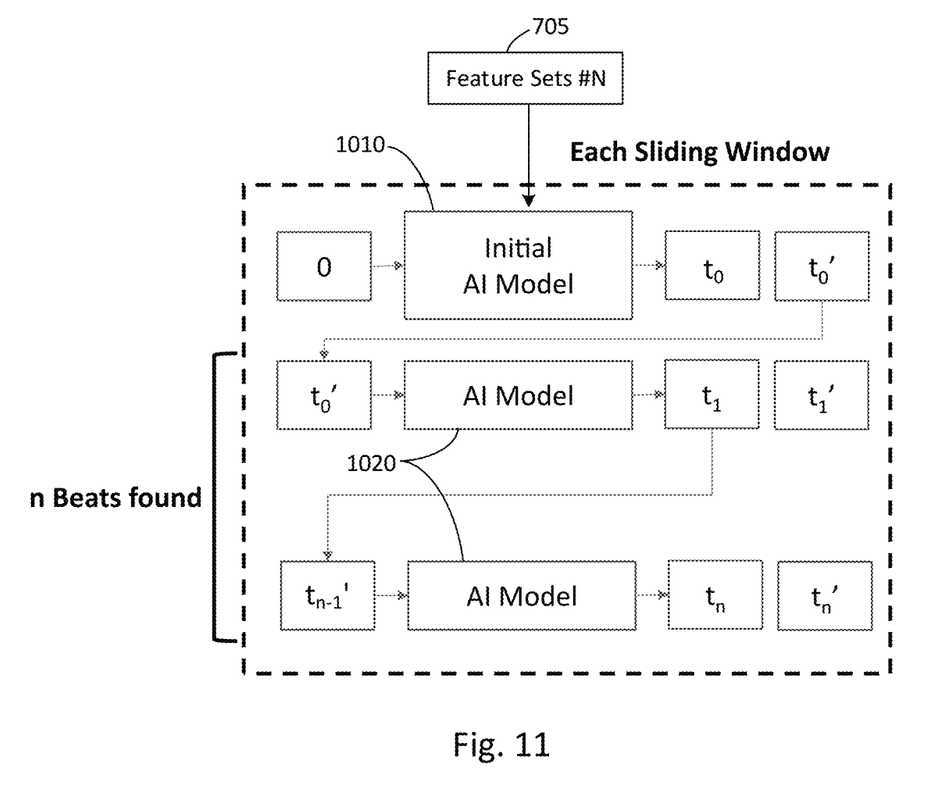
FIG. 11 is a block diagram corresponding to the data inferencing process shown in FIG. 8.

FIG. 11 is a block diagram corresponding to the data inferencing process shown in FIG. 8. As shown in FIG. 11, the feature dataset 705 is inputted to the initial AI model 1010 which detects a pilot peak time to immediately before a predetermined detection zone and a next peak time $t_0'$ which is a first peak time within the detection zone. The initial AI model 1010 may be adjusted according to the experience in detecting the peak times $t_0$ and $t_0'$, and an adjusted AI model 1020 may be used for detecting subsequent peak times. With a previous detected peak time as an input, the AI model 1020 detect subsequent peak times from the feature dataset. For example, the peak time $t_0'$ is inputted into the AI model 1020 which detects next peak times $t_1$ and $t_1'$. An IBI can then be calculated by subtracting a current peak time $t_1$ from a next peak time $t_1'$. Such process continues until all n beats are found in the detection zone.

Figure 12A:
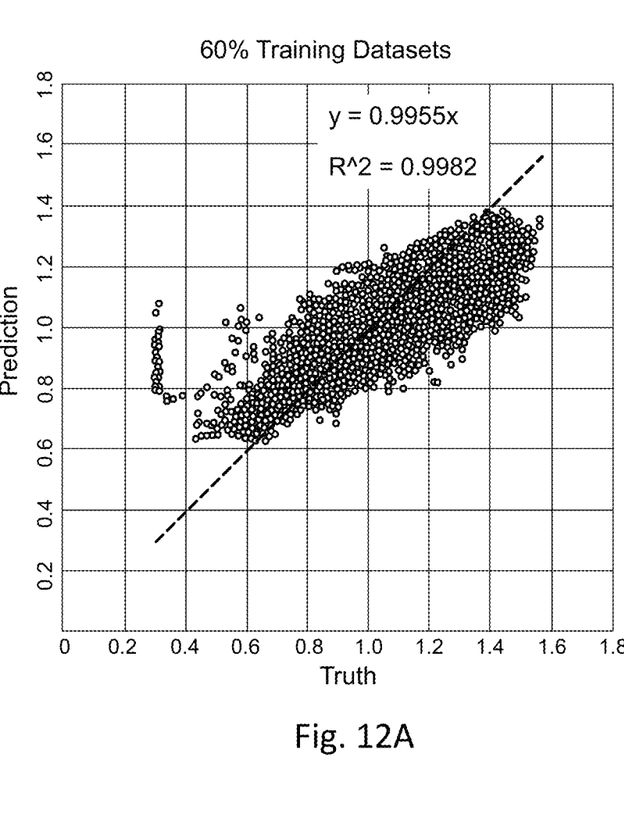
FIGS. 12A and 12B illustrate accuracies of the training and inferencing of the present disclosure.
Figure 12B:
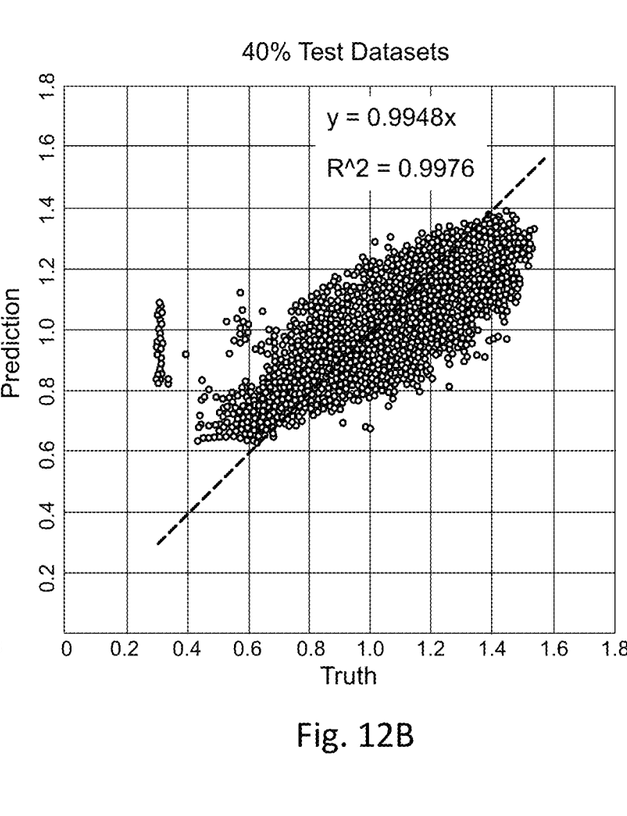

FIGS. 12A and 12B illustrate accuracies of the training and inferencing of the present disclosure. To verify the training and inferencing processes, a total of 377,494 patient's data are collected with 60% of the data used for the training process (training datasets) and 40% of the data used for the inferencing process (test datasets). The patient's data include both ECG IBI measurements regarded as the target values or truth (y-axis), and the radar IBI measurements extracted through the AI processes of the present disclosure regarded as prediction values (x-axis). The training datasets are used to train an AI model which is then used on the test datasets to extract IBI data corresponding to the test datasets.

Regression analysis is employed to analyze a relationship between the target values and the prediction values. Regression analysis is represented on the plot as a curve/line segment that strives to fit all the data points. A coefficient of determination ($R^2$) represents the ratio of the variation value of the regression mode to all yi variations, and the larger $R^2$, the greater the proportion of the regression mode that can explain the total yi variation. Therefore, the closer $R^2$ is to 1.0, the more explanatory the pattern is. In statistics, linear regression is a regression analysis that uses a least squares function called a linear regression equation to model the relationship between one or more independent and regent variables.

Referring to FIG. 12A, for the training datasets, the target value (y) and the prediction value (x) follows a linear equation of y=1.1344x−0.1282 (the dotted line) with $R^2$=0.9357. Referring to FIG. 12B, for the test datasets, the target value (y) and the prediction value (x) follows a linear equation of y=1.1247x−0.1186 (the dotted line) with $R^2$=0.9077. As shown in FIGS. 12A and 12B, the closer the dots to the dotted line, the more accurate the prediction values to the target values. The regression analysis is instrumental to improving accuracy of the AI model training process.

Figure 13:
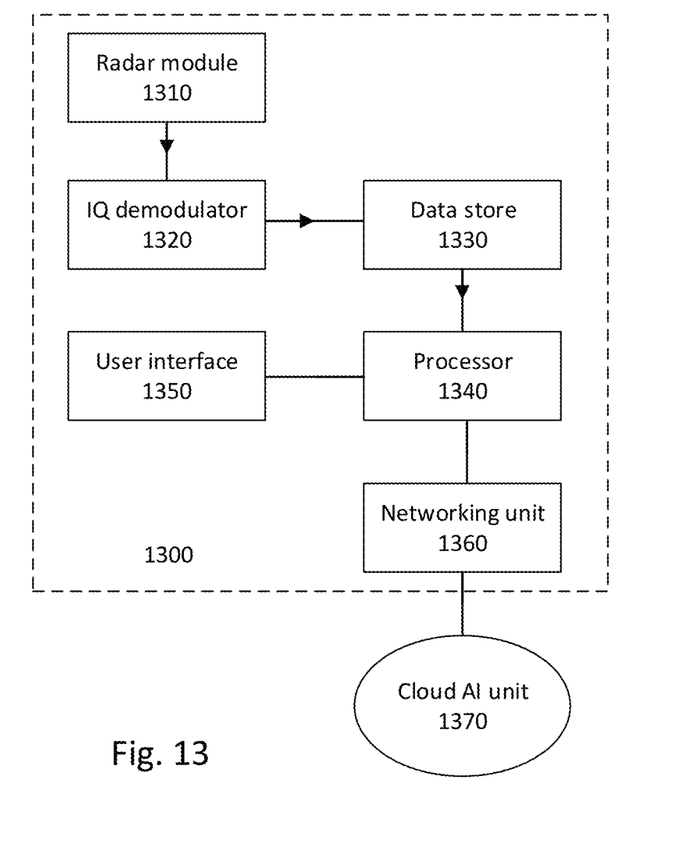
FIG. 13 is a block diagram illustrating a radar HRV measurement system working with a cloud based AI unit according to embodiments of the present disclosure.

FIG. 13 is a block diagram illustrating a radar HRV measurement system 1300 working with a cloud based AI unit 1370 according to embodiments of the present disclosure. The HRV measurement system 1300 employs a radar module 1310 as a touchless patient's chest displacement detector. Radar raw data are processed by an exemplary IQ demodulator 1320 to obtain feature datasets from the raw data which are then stored in a data store 1330. A processor 1340 working with a user interface 1350 controls data sampling by the radar module 1310 and a networking unit 1360 to communicate with a cloud based AI unit 1370, which is exemplarily hosted in a remote data center. The processor 1340 controls transmission of the feature datasets to the cloud based AI unit 1370, and receives AI predicted HRV data to be displayed on the user interface 1350. Alternatively, the data store 1330 stores the pretrained AI model and instructions associated with a neural network, and the processor 1360 runs the inferencing process based on the local stored AI model and neural network.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In certain embodiments, a particular software module or component may comprise disparate instructions stored in different locations of a memory device, which together implement the described functionality of the module. Indeed, a module or component may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, Software modules or components may be located in local and/or remote memory storage devices. In addition, data being tied or rendered together in a database record may be resident in the same memory device, or across several memory devices, and may be linked together in fields of a record in a database across a network.

Although the disclosure is illustrated and described herein as embodied in one or more specific examples, it is nevertheless not intended to be limited to the details shown, since various modifications and structural changes may be made therein without departing from the spirit of the disclosure and within the scope and range of equivalents of the claims. Accordingly, it is appropriate that the appended claims be construed broadly and, in a manner, consistent with the scope of the disclosure, as set forth in the following claims.

What is claimed is:

1. An apparatus for detecting heartbeat, the apparatus comprising:
   a first and second sensor configured to simultaneously detect displacements of an object to generate a first and second signal, respectively, corresponding to the displacements, the first sensor detecting the displacements without contacting the object, the second sensor detecting the displacements by contacting the object;
   a demodulator configured to receive and convert the first signal into corresponding in-phase (I) and quadrature (Q) components;
   a first data processing unit configured to:
      extract phase and amplitude data from the I and Q components,
      extract phase difference and amplitude difference data from the extracted phase and amplitude data,
      generate a first feature dataset from the phase, amplitude, phase difference and amplitude difference data;
   a second data processing unit configured to:
      detect peak times in the second signal, and
      generate labeling data from the detected peak times; and
   a first neural network configured to receive the first feature dataset and the labeling data for training a model,
   wherein the trained model is used to infer inter beat intervals from a second feature dataset extracted from the first signal.

2. The apparatus of claim 1, wherein the first sensor is a radar unit configured to transmit a radio wave on the object and detect a reflection of the radio wave.

3. The apparatus of claim 1, wherein the object displaces corresponding to heartbeat of a living creature.

4. The apparatus of claim 1, wherein inferring the inter beat intervals includes detecting peak times in the second feature dataset by the first neural network.

5. The apparatus of claim 4, wherein the detecting peak times includes searching for patterns of the trained model in the second feature dataset by the first neural network.

6. The apparatus of claim 1, wherein the peak times are detected sequentially, wherein the inter beat intervals are calculated from neighboring peak times.

7. The apparatus of claim 1 further comprising a processor configured to run the first neural network.

8. The apparatus of claim 1, wherein the first neural network and the model reside in a remote data center.

9. The apparatus of claim 8 further comprising a networking unit configured to transmit the first and second feature dataset to the remote data center.

10. The apparatus of claim 1, wherein the model is developed by a second neural network by comparing peak times extracted from the first feature dataset with peak times measured by a reference measurement on the object, wherein the first and second neural network are of the same type.

11. The apparatus of claim 10, wherein the reference measurement is an electrocardiogram (ECG).

12. The apparatus of claim 10, wherein the first feature dataset is organized into a first and second overlapped detection time zone.

13. The apparatus of claim 12, wherein a peak time immediately prior to the first detection time zone is used as a pilot peak time for the second neural network for training the model.

14. A method for detecting heartbeat, the method comprising:
   Simultaneously detecting, by a first and second sensor, displacements of an object to generate a first and second signal, respectively, corresponding to the displacements, the first sensor detecting the displacements without contacting the object, the second sensor detecting the displacements by contacting the object;
   demodulating, by a demodulator, the first signal into corresponding in-phase (I) and quadrature (Q) components;
   extracting, by a first data processing unit, phase and amplitude data from the I and Q components;
   extracting, by the first data processing unit, phase difference and amplitude difference data from the extracted phase and amplitude data;
   generating, by the first data processing unit, a first feature dataset from the phase, amplitude, phase difference and amplitude difference data; and
   detecting, by a second data processing unit, peak times in the second signal;
   generating, by the second data processing unit, labeling data from the detected peak times;
   training, by a first neural network, a model with the first feature dataset and the labeling data,
   wherein the trained model is used to infer inter beat intervals from a second feature dataset extracted from the first signal.

15. The method of claim 14, wherein the first sensor is a radar unit configured to transmit a radio wave on the object and detect a reflection of the radio wave.

16. The method of claim 14, wherein inferring the inter beat intervals includes detecting peak times in the second feature dataset by the first neural network searching for patterns of the trained model in the second feature dataset.

17. The method of claim 14, wherein the first neural network and the model reside in a remote data center.

18. The method of claim 14, wherein the pre-trained model is developed by a second neural network by comparing peak times extracted from the first feature dataset with peak times measured by an electrocardiogram (ECG) measurement on the object, wherein the first and second neural network are of the same type.

19. The method of claim 14, wherein the first feature dataset is organized into a first and second overlapped detection time zone.

20. An apparatus for detecting heartbeat, the apparatus comprising:
   a first and second sensor configured to simultaneously detect displacements of an object to generate a first and second signal, respectively, corresponding to the displacements, the first sensor detecting the displacements without contacting the object, the second sensor detecting the displacements by contacting the object, wherein the object displaces corresponding to heartbeat of a living creature;

a demodulator configured to receive and convert the first signal into corresponding in-phase (I) and quadrature (Q) components;

a first data processing unit configured to:
  extract phase and amplitude data from the I and Q components,
  extract phase difference and amplitude difference data from the extracted phase and amplitude data,
  generate a first feature dataset from the phase, amplitude, phase difference and amplitude difference data;

a second data processing unit configured to:
  detect peak times in the second signal, and
  generate labeling data from the detected peak times; and a neural network configured to receive the first feature dataset and the labeling data for training a model, wherein the trained model is used to infer inter beat intervals from a second feature dataset extracted from the first signal by searching for patterns of the trained model in the second feature dataset for detecting peak times.

* * * * *